(12) United States Patent
Wills et al.

(10) Patent No.: US 6,685,918 B1
(45) Date of Patent: Feb. 3, 2004

(54) ORAL CLEANSING PRODUCT

(75) Inventors: Kevin John Wills, Buckinghamshire (GB); Iain Stewart Duncan, Fife (GB)

(73) Assignee: Alcan International Limited, Montreal (CA)

( * ) Notice: Subject to any disclaimer, the term of this patent is extended or adjusted under 35 U.S.C. 154(b) by 0 days.

(21) Appl. No.: 10/111,178

(22) PCT Filed: Nov. 27, 2000

(86) PCT No.: PCT/GB00/04483

§ 371 (c)(1),
(2), (4) Date: Jul. 12, 2002

(87) PCT Pub. No.: WO01/37796

PCT Pub. Date: May 31, 2001

(30) Foreign Application Priority Data

Nov. 26, 1999 (GB) ............................................ 99228055

(51) Int. Cl.$^7$ ............................ A61K 7/16; A61K 7/18; C09C 1/68

(52) U.S. Cl. ............................ 424/49; 424/52; 51/293; 51/309

(58) Field of Search ...................................... 424/49–58

(56) References Cited

U.S. PATENT DOCUMENTS

| | | | | |
|---|---|---|---|---|
| 2,010,910 A | * | 8/1935 | Atkins | 167/93 |
| 2,550,207 A | * | 4/1951 | Tainter et al. | 117/93 |
| 3,060,098 A | * | 10/1962 | Gershon | 167/93 |
| 3,121,623 A | * | 2/1964 | Nesin | 51/293 |
| 3,957,968 A | * | 5/1976 | Cordon | 424/49 |
| 4,060,599 A | * | 11/1977 | Cordon | 424/49 |
| 4,212,856 A | * | 7/1980 | Hoyles | 424/52 |
| 4,582,697 A | * | 4/1986 | Cristol et al. | 423/629 |
| 4,623,364 A | * | 11/1986 | Cottringer et al. | 51/309 |
| 4,632,826 A | * | 12/1986 | Ploger et al. | 424/52 |
| 4,986,981 A | * | 1/1991 | Glace et al. | 424/50 |
| 5,039,514 A | * | 8/1991 | Evans et al. | 424/52 |
| 5,383,945 A | * | 1/1995 | Cottringer et al. | 51/309 |

FOREIGN PATENT DOCUMENTS

| | | |
|---|---|---|
| EP | 0002386 | 6/1979 |
| EP | 0328407 | 8/1989 |
| FR | 2534898 | 4/1984 |
| GE | 2409757 | 9/1975 |

* cited by examiner

*Primary Examiner*—Shep K. Rose
(74) *Attorney, Agent, or Firm*—Cooper & Dunham LLP

(57) ABSTRACT

There is disclosed an oral cleansing product comprising as an abrasive an alumnina in the form of particles having $d_{10}$ below 3.5 μm, $d_{50}$ below 1.0 μm, and a specific surface area below 6 m$^2$/g.

13 Claims, No Drawings

ORAL CLEANSING PRODUCT

International standard ISO11609 of 1995 contains the following definitions:

Dentifrice: any substance or combination of substances specially prepared for the public for cleaning the accessible surfaces of teeth.

Toothpaste: any semi-solid dentifrice preparation presented in the form of a paste, cream or gel.

This invention is concerned with oral cleansing products, including dentifrices and (to the extent that they are not classed as dentifrices) chewing gum and candy.

An oral cleansing product invariably contains an abrasive powder for cleaning purposes. The cleaning and abrasive properties of the oral cleansing product depend on the concentration of the powder, on the Moh's hardness of the abrasive, and on the shape and particle size and size distribution of the powder. The cleaning effect of an oral cleansing product concerns its effectiveness in removing adventitious stains and other deposits from the surface of teeth and other parts of oral cavity. The abrasive effect or abrasivity concerns undesired removal of surface components of teeth including enamel and dentine, and undesired damage in the oral cavity. An oral cleansing product having a high cleaning effect generally has a rather high abrasivity, and vice versa. ISO11609 provides methods for testing abrasivity and sets limits on dentifrices marketed in Europe. An earlier British standard BS5136 of 1981 also sets limits on abrasivity by comparison with a standard reference toothpaste, which is also used as a reference in ISO11609, and which has the formulation:

Precipitated calcium carbonate 40% w/w.

Glycol 25% w/w

Sodium carboxymethylcellulose 1.40% w/w

Dodecyl sodium sulphate 1.00% w/w

Sodium silicate (80° TW of approximately pH 7) 0.05% w/w

Saccharin sodium 0.15% w/w

Formalin (40% (m/m) formaldehyde) 0.10 w/w

Peppermint flavouring 0.80% w/w

Water 33.05% w/w

Abrasive powders used or contemplated for use in oral cleansing products include silicas, including gels and precipitates, sodium bicarbonate, calcium and magnesium carbonates, calcium phosphates, alumina and hydrates thereof, aluminosilicates, aluminium and magnesium silicates, and thermosetting urea-formaldehyde and other plastics materials. There is a need in the industry for an abrasive for inclusion in oral cleansing products, which provides good cleaning properties, in particular stain removal, while showing relatively low abrasivity. In particular, there is a need for an abrasive which can be incorporated in a concentration large enough to provide an excellent cleaning effect with low abrasivity which nevertheless complies with the abrasivity requirements of the above-stated standard specifications. This invention addresses that need.

U.S. Pat. No. 3,957,968 teaches the use of flat flakes of α-aluminium oxide in toothpaste. The flakes have a median particle size of 2 to 7 $\mu$m. U.S. Pat. No. 4,060,599 discloses the use of a finer aluminium oxide (median 1 to 2 $\mu$m) and specifically uses Reynolds RC152DBM which has a median size of around 1.7 $\mu$m.

U.S. Pat. No. 4,632,826 teaches the use of a weakly calcined alumina polishing agent. This polishing agent consists of 10% to 50% by weight γ aluminium oxide and 50% to 90% by weight α aluminium oxide.

GB-A-2155333 teaches the use of calcium hydrogenphosphate anhydride and an aluminium oxide having an average particle size of 0.5 $\mu$m to 10 $\mu$m. The alumina has a high a-content, as measured by X-ray diffraction.

WO-A-95/33441 teaches the use of cationically charged colloids of a metal compound. The colloid has a particle size of 0.001 $\mu$m to 0.2 $\mu$m.

GB-A-2037162 and GB-A-2009596 disclose the use of hydrated aluminas in dentifrice products.

The phrase "alumina" is sometimes loosely used to cover a number of aluminium oxide, oxide hydroxide and trihydroxide compounds. The correct designations and some crystalline phases are shown below:

| Mineral Name | Chemical Composition | Accepted Crystallographic and Chemical Designation |
|---|---|---|
| Gibbsite | Aluminium trihydroxide | γ - Al(OH)$_3$ |
| Bayerite | Aluminium trihydroxide | α - Al(OH)$_3$ |
| Nordstrandite | Aluminium trihydroxide | Al(OH)$_3$ |
| Boehmite | Aluminium oxide hydroxide | γ - AlOOH |
| Diaspore | Aluminium oxide hydroxide | α - AlOOH |
| Corundum | Aluminium oxide | α - Al$_2$O$_3$ |

This invention is concerned with alumina that is essentially Corundum. Corundum is produced by calcination of aluminium trihydroxides and oxide hydroxides. Depending on the form of aluminium trihydroxide and oxide hydroxide starting material, a number of forms of alumina (often described as activated aluminas) are produced before corundum is formed. Another form of alumina chemical is aluminium hydroxide gel, which is often formed by the neutralisation of an aluminium salt solution.

The invention provides an oral cleansing product comprising as an abrasive an alumina in the form of particles having $d_{10}$ below 3.5 $\mu$m, $d_{50}$ below 1.0 $\mu$m, and specific surface area below 6 m$^2$/g.

According to a further aspect of the present invention, there is provided the use of alumina as an abrasive in an oral cleansing product, wherein the alumina is in the form of particles having $d_{10}$ below 3.5 $\mu$m, $d_{50}$ below 1.0 $\mu$m, and a specific surface area below 6 m$^2$/g.

According to a further aspect of the present invention, there is provided the use of alumina as a whitening agent in an oral cleansing product, wherein the alumina is in the form of particles having $d_{10}$ below 3.5 $\mu$m, $d_{50}$ below 1.0 $\mu$m, and a specific surface area below 6 m$^2$/g. In this way the alumina used may serve the purpose of replacing titania or the like in conventional products, thus resulting in a cost saving.

The surface area is measured by the following method. A sample of alumina of sufficient weight to give an estimated surface area of about 0.5 to 25 m$^2$ is degassed in a Micrometrics Desorb 2300B at about 150° C. until a stable reading is obtained. The sample is then transferred to a Micrometrics Flowsorb II 2300, cooled and immersed in a mixture of 30% N and 70% He gas. The total amount of N absorbed is measured from the change in thermal conductivity of the gas mixture preferably during desorption as the temperature is raised again to room temperature. Surface area per gram is then calculated from the total gas absorbed and the weight of the sample.

The particle size is measured as follows. Particle size distribution of a sample of alumina is measured in a Sedigraph 5100 instrument supplied, by Micrometrics Products.

The abrasive is preferably an anhydrous alumina, generally a calcined alumina or alternatively a tabular or fused alumina. Calcination is effected at a temperature of at least 900° C. Higher calcination temperatures result in harder products. The alumina used in this invention is preferably fairly hard, such as may be obtained by calcination at above 1000° C. The alumina in this invention is an α-alumina. Preferably, the α content is greater than 90%, preferably greater than 93%, even more preferably greater than 95%, as measured by X-ray diffraction. In a preferred embodiment, the γ-content is less than 1%.

The abrasive is used in the form of particles having $d_{10}$ below 3.5 μm, preferably below 2.5 μm. ($d_{10}$, $d_{50}$ and $d_{90}$ are used in conventional manner to indicate that 10, 50 or 90 wt % of the product has a particle size above the stated value). Preferably, the alumina abrasive is a sub-micron product, having $d_{50}$ of 0.1–1.0 μm. Preferably the alumina abrasive has a relatively narrow particle size distribution, e.g. with $d_{10}$ being no greater than four times $d_{50}$.

The alumina abrasive has a specific surface area below 6 $m^2/g$, preferably in the range of 4.5–5.0 $m^2/g$. The specific surface area is related to the aforesaid parameters of hardness (harder products have lower specific surface areas) and particle size (more finely divided products have larger specific surface areas).

Alumina products of the kind described are readily available commercially, for they are produced in substantial quantities mainly for use in refractories and ceramics. Grinding may conveniently be effected by fluid energy or vibratory milling (micronising) or preferably by ball milling.

When an abrasive powder has excellent stain removal properties in one toothpaste, it is generally the case that it will be found to have excellent stain removal properties in other oral cleansing products. Although the abrasivity of an oral cleansing product does depend to a significant extent on the whole formulation, and not merely on the nature and concentration of the abrasive present in it, nevertheless an abrasive which shows high or low abrasivity in one formulation may generally be expected to show correspondingly high or low abrasivity in others.

The alumina abrasive is preferably present in the oral cleansing product at a concentration of 1–15% w/w, preferably higher than 2%, even more preferably higher than 3%, e.g. 3–12% w/w. Toothpastes and other oral cleansing products include a wide variety of components in a wide variety of concentrations. The alumina should be compatible with other ingredients. The following list is intended to be exemplary rather than definitive or restrictive.

Toothpastes are generally water-based. Other dentifrice formulations are typically water-based or are supplied dry and require water for activation. Chewing gums and candies are generally based on natural or synthetic elastomers or gum bases.

A binder or thickener is generally present. Examples of suitable materials are carboxyvinyl polymers, carrageenan, hydroxyethyl cellulose and water soluble salts of cellulose ethers such as sodium carboxymethylcellulose and sodium carboxymethyl hydroxyethyl cellulose. Natural gums and colloidal silica or silicate materials can also be used. Binders or thickeners are generally present in an amount from about 0.15 to about 5.0% w/w of the total composition.

A humectant is also generally used to keep the formulation from hardening on exposure to air. Examples of suitable humectants are glycerine, sorbitol, xylitol, polyethylene glycols and propylene glycol. Humectants are generally present in an amount from about 10% to about 70% w/w of the weight of the composition.

One or more particulate materials, regarded as abrasives or abrasive polishers or fillers, are also present. The alumina abrasive described above is one such, but others may also be present as noted above. Examples are:

Silicas, including gels and precipitates, sodium bicarbonate, calcium and magnesium carbonates, dicalcium phosphate dihydrate, alumina and hydrates thereof, aluminosilicates, aluminium and magnesium silicates, and thermosetting urea-formaldehyde and other plastics materials. It is preferred that the alumina is not present in combination with calcium hydrogenphosphate anhydride.

Abrasives are generally present at a level of about 10% to about 70%, preferably from about 15% to about 25%, w/w of the formulation.

A source of fluoride ion is preferably provided. Regulatory authorities in various countries may stipulate a maximum and/or a minimum total fluoride ion concentration.

Chewing gums are generally based on one or more of: natural and synthetic elastomers e.g. polybutene or polyisobutene, which may be softened with vegetable fats or oils or plasticisers; waxes; humectants such as xylitol; natural and synthetic resins and gum bases such as chicle.

Other components which may also be included in oral cleansing products in accordance with conventional practice, include sweeteners, flavours, colours, peroxides or other bleaching agents, anti-calculus agents, anti-plaque agents, anti-bacterial agents, preservatives and effervescence generators.

Toothpaste and other oral cleansing products may be manufactured by conventional techniques. The alumina abrasives with which this invention is concerned are rather easy to incorporate for, unlike some other abrasive powders, they are generally not prone to lumping.

Here is an example of a toothpaste formulation:

Dicalcium phosphate 40% w/w
Alumina 10%
Sorbitol 25%
Polyethylene glycol 2%
Carboxymethylcellulose 1.1%
Sodium Saccharin 0.2%
Sodium Lauryl Sulphate 1.5%
Benzoic Acid 0.15%
Sodium Benzoate 0.2%
Water 19.5%

This formulation based on dicalcium phosphate polishing agent/filler, has been used to test the properties of various alumina abrasives. In the experimental section below, a different formulation based on a silica polishing agent/filler was used. Although the results obtained with the two formulations were different in absolute terms, they were generally the same in relative terms, i.e. any particular alumina abrasive generally had the same or a similar effect on the properties of both formulations. This justifies the assertion that an abrasive showing valuable properties in one toothpaste may reasonably be expected to show corresponding valuable properties in other oral cleansing products.

The alumina abrasives used in the experimental section below are either commercial products or development products (designated BAX). available from Alcan Chemicals Limited, and are here identified by means of their trade names. This invention is based on the discovery that the development product BAX842 has unexpectedly and outstandingly good properties.

EXAMPLE 1

In this example, a silica-based toothpaste was used. The formulation Was as shown in Table 1.

TABLE 1

Silica-based toothpaste formulation

| Ingredient | % w/w |
|---|---|
| Polyethylene Glycol | 3.0 |
| Sodium carboxymethyl cellulose | 0.6 |
| Deionised Water | 7 |
| Sodium Fluoride | 0.243 |
| 10% Sorbitol | 56.107 |
| Sodium Saccharin | 0.3 |
| Titanium Dioxide | 0.3 |
| Abrasive Silica | 20.5 |
| Flavour | 0.75 |
| Sodium Lauryl Sulphate | 1.2 |
| Alumina | 10.0 |
| Total | 100 |

The alumina products used in this example are given in Table 2.

TABLE 2

| Product | Mineralogy/ Milling route | SSA m²/g | Sedigraph $d_{10}$ | $d_{50}$ | $d_{90}$ |
|---|---|---|---|---|---|
| X | Alumina/micronised | 1.3 | 5.19 | 3.11 | 1.4 |
| RA207LS | Alumina/ball milled | 8.2 | 1.01 | 1.4 | 0.18 |
| BAX888 | Alumina/ball milled | 6.8 | 1.41 | 0.48 | 0.27 |
| BAX842 | Alumina/ball milled | 4.8 | 2.35 | 0.62 | 0.36 |
| BAX904 | Alumina/ball milled | 6.1 | 2.07 | 0.51 | 0.25 |
| PA2 (1) | Alumina/ball milled | 6.7 | 8.24 | 1.18 | 0.47 |
| PA2 (2) | Alumina/micronised | 4.4 | 6.83 | 0.99 | 0.51 |
| MA250 | Alumina/micronised | 4.6 | 11.05 | 1.29 | 0.49 |
| BAX 985A | Alumina/ball milled | 5.9 | 3.23 | 0.53 | 0.28 |
| BAX 985B | Alumina/ball milled | 6.6 | 2.47 | 0.49 | 0.25 |

For stain removal, samples were subjected to an in-vitro test developed and performed by the Health Science Research Centre at Indiana University—Purdue University. This test involves staining teeth using a broth containing instant coffee, instant tea, gastric mucin3 and a micrococcus leteus culture. The colour of the stained teeth is measured using a Minolta colourmeter. The teeth are then brushed with the toothpaste and the colour measured. A measurement of stain removal is then calculated.

The enamel abrasivity (Designated REA) was measured by Missouri Analytical Laboratories, using a method described by R J Grabenstetter et al. (J D Res. Vol. 37, November–December 1958, No. 6, pages 1060–8).

The abrasivity and stain removal results are shown in Table 3.

TABLE 3

Abrasivity and stain removal results

| | Enamel Abrasivity REA Value | Stain Removal % |
|---|---|---|
| X | 149 | 55 |
| RA207LS | 45 | 42 |
| BAX888 | 53 | 42 |
| BAX842 | 46 | 50 |
| BAX904 | 58 | 40 |
| PA 2(1) | 70 | 43 |
| PA2 (2) | 80 | 37 |
| MA250(3) | 110 | 54 |
| BAX 985A | 86 | 50 |
| BAX 985B | 77 | 42 |

Discussion

The comparative performance of the aluminas in terms of abrasivity (REA value) and stain removal is shown in FIG. 1. BAX 842 is outstanding.

The relationship between particle size $d_{10}$ and enamel abrasivity is shown in FIG. 2. For the ball milled products, it can be seen in FIG. 2 that there is a linear relationship ($R^2=0.96$, equation $y=18.985x+25.109$) between REA value and $d_{10}$ with REA falling as the $d_{10}$ decreases. BAX842 does not fit this linear relationship as the abrasivity is much less than would be expected for its $d_{10}$, i.e. for a $d_{10}$ value of 2.35 μm, the linear regression equation calculates an enamel abrasivity of 69 versus 46 obtained with BAX842. There is no relationship between enamel abrasivity and $d_{10}$ for the micronised aluminas. The relationship between stain removal and $d_{10}$ for the ball milled and micronised aluminas shows significant scatter in performance with no linear relationship.

EXAMPLE 2

Sugar-free chewing gums to the formulations shown below were prepared using the following method.

The sugar-free gum base was heated in an oven at 70–75° C. for approximately 2 hrs until it softened. A Z-blade mixer was preheated to 45° C. and the softened gum base was added. The mannitol powder was added in small doses and was mixed until well combined. 60% of the total Sorbitol powder was added in small doses until it was well combined. Where applicable, the alumina was added in small doses and again mixed until well combined. The lecithin was then added and mixed until well combined. A further 20% of the total Sorbitol powder was added in small doses and mixed until well combined. 50% of the total glycerine was added and mixed until well combined. A further 10% of the Sorbitol powder was added until well combined. A remaining 50% of the glycerine was added until well combined. The maltitol syrup was added in small doses until well combined. The remaining 10% of the total Sorbitol powder was then added in small doses and mixed until well combined. During the mixing operation, the mixer temperature was maintained at 45° C.

The product was removed from the mixer and transferred to a marble slab, which had been pre-dusted with mannitol. The product was covered with grease-proof paper dusted with mannitol powder and rolled by hand using a pin roll until a uniform thickness of approximately 1 cm was achieved. The product was then passed through a mechanical sheeter whilst gradually reducing the depth until a thickness of approximately 2 mm was obtained. Using roll cutters, the product was cut into strips approximately 1 cm wide. Using a knife, the strips were cut into 5 cm lengths. The gum was then wrapped in paper-lined foil and stored at 20–25° C.

TABLE 4

Chewing gum formulations (Example 2)

| Ingredient | Control (%) | Gum 1 (%) | Gum 2 (%) | Gum 3 (%) | Gum 4 (%) | Gum 5 (%) |
|---|---|---|---|---|---|---|
| Gum base | 28.95 | 28.95 | 28.95 | 28.95 | 28.95 | 28.95 |
| Sorbitol | 50.10 | 40.10 | 40.10 | 45.10 | 47.10 | 49.10 |
| Maltitol syrup | 8.15 | 8.15 | 8.15 | 8.15 | 8.15 | 8.15 |
| Glycerine | 7.15 | 7.15 | 7.15 | 7.15 | 7.15 | 7.15 |
| Mannitol | 5.15 | 5.15 | 5.15 | 5.15 | 5.15 | 5.15 |
| Lecithin | 0.5 | 0.5 | 0.5 | 0.5 | 0.5 | 0.5 |
| Alumina X | — | 10 | — | — | — | — |
| BAX842 | — | — | 10 | 5 | 3 | 1 |

Alumina Products Tested

The alumina products tested in this example are given in Table 5:

| Product | Milling Route | SSA ($m^2/g$) | Sedigraph psd ($\mu m$) D10 | D50 | D90 |
|---|---|---|---|---|---|
| BAX842 | Ball milled | 4.8 | 2.3 | 0.62 | 0.36 |
| X | Micronised | 1.3 | 5.19 | 3.11 | 1.4 |

Observations

All the formulations gave final products with an homogeneous appearance and a texture and consistency expected for typical chewing gum. The alumina formulations were whiter than the control product. Also as the alumina addition level increased the gum became more manageable and less sticky.

Stain Removal Performance

The stain removal performance of the chewing gum formulations was measured at Indiana University—Purdue University. The test involves treating stained teeth for 60 minutes with 5 g of chewing gum using mechanical mastication; the gum is changed every 20 minutes. The colour of the teeth before and after chewing was measured using a Minolta CM-5031 spectrophotometer. The overall change in stain (delta E value) is calculated from the CIE L*a*b*equation.

The results for the formulations are shown in Table 6:

| Product | Alumina Addition Level | Delta E Value, % |
|---|---|---|
| Control | 0% | 7.5 |
| X | 5% | 9.6 |
| BAX842 | 1% | 10.1 |
| BAX842 | 3% | 11.7 |
| BAX842 | 5% | 13.7 |
| BAX842 | 10% | 35.2 |

The enamel abrasivity values for these aluminas in toothpaste is shown below.

| Product | Enamel Abrasivity, REA |
|---|---|
| X | 149 |
| BAX842 | 46 |

It is surprising that BAX842 despite its finer particle size and lower enamel abrasivity gave greater stain removal performance than alumina X.

EXAMPLE 3

Sugar-free chewing gums to the formulations shown in Table 7 were prepared in the same manner as described in Example 2. These experiments used a different gum base and substituted 0.25% Sorbitol by peppermint flavouring. The characteristics of the aluminas used in these experiments are shown in Table 2 in Example 1.

TABLE 7

Chewing gum formulations (Example 3)

| Ingredient | Gum 1 (%) | Gum 2 (%) | Gum 3 (%) | Gum 4 (%) | Gum 5 (%) |
|---|---|---|---|---|---|
| Gum base | 28.95 | 28.95 | 28.95 | 28.95 | 28.95 |
| Sorbitol | 39.85 | 39.85 | 39.85 | 39.85 | 39.85 |
| Maltitol syrup | 8.15 | 8.15 | 8.15 | 8.15 | 8.15 |
| Glycerine | 7.15 | 7.15 | 7.15 | 7.15 | 7.15 |
| Mannitol | 5.15 | 5.15 | 5.15 | 5.15 | 5.15 |
| Lecithin | 0.5 | 0.5 | 0.5 | 0.5 | 0.5 |
| Peppermint flavour | 0.25 | 0.25 | 0.25 | 0.25 | 0.25 |
| Alumina Y | 10 | — | — | — | — |
| BAX842 | — | 10 | — | — | — |
| BAX888 | — | — | 10 | — | — |
| BAX985A | — | — | — | 10 | — |
| BAX904 | — | — | — | — | 10 |

As described in Example 2, the stain removal performance of the chewing gum was measured at Indiana University—Purdue University. The results are shown in Table 8.

TABLE 8

Stain removal results for chewing gum formulations (Example 3)

| | Alumina | | | | |
|---|---|---|---|---|---|
| | X | BAX842 | BAX888 | Blend 5 | BAX904 |
| Stain Removal Performance, % | 11.0 | 13.5 | 9.9 | 8.8 | 8.9 |

It is surprising that despite being significantly finer than alumina X, BAX842 gave a >20% increase in stain removal performance. Also, compared with other sub-micron alumina products (BAX888, BAX985A and BAX904) BAX842 gave a significantly higher stain removal performance.

What is claimed is:

1. An oral cleansing product comprising as an abrasive in a formulation of the oral cleansing product an alumina in the form of particles having $d_{10}$ below 3.5 $\mu m$, $d_{50}$ below 1.0 $\mu m$, and a specific surface area below 6 $m^2/g$, wherein the alumina is at least 90% α-alumina calcined at a temperature of at least 900° C.

2. The oral cleansing product of claim 1 wherein $d_{10}$ is below 2.5 $\mu m$.

3. The oral cleansing product of claim 1 wherein the specific surface area is 4.5–5.0 m$^2$/g.

4. The oral cleansing product of claim 1, wherein the particles have d$_{50}$ of 0.1–1.0 µm.

5. The oral cleansing product of claim 4, wherein the ratio of d$_{10}$ to d$_{50}$ is not more than 4.0.

6. The oral cleansing product of claim 1, wherein the abrasive is present in a proportion of 1–15% w/w.

7. The oral cleansing product of claim 1, wherein the alumina is ball-milled.

8. The oral cleansing product of claim 1, wherein the alumina has an α content of greater than 90%.

9. The oral cleansing product of claim 8, wherein the alumina has an α content greater than 93%.

10. The oral cleansing product of claim 1, which is a dentifrice.

11. The oral cleansing product of claim 1, which is a chewing gum.

12. An oral cleansing method comprising cleaning parts of an oral cavity with an oral cleansing product containing alumina as an abrasive, wherein the alumina is in the form of particles having d$_{10}$ below 3.5 µm, d$_{50}$ below 1.0 µm, and a specific surface area below 6 m$^2$/g, and wherein the alumina is at least 90% α-alumina calcined at a temperature of at least 900° C., such that he oral cleansing product is effective in removing deposits from dental surfaces without undesired removal of dental surface components.

13. An oral cleansing method comprising cleaning parts of an oral cavity with an oral cleansing product containing alumina as a whitening agent, wherein the alumina is in the form of particles having d$_{10}$ below 3.5 µm, d$_{50}$ below 1.0 µm, and a specific surface area below 6 m$^2$/g, and wherein the alumina is at least 90% α-alumina calcined at a temperature of at least 900° C., such that the oral cleansing product is effective in removing deposits from dental surfaces without undesired removal of dental surface components.

* * * * *